United States Patent
Farwick et al.

US006777206B2

(10) Patent No.: US 6,777,206 B2
(45) Date of Patent: Aug. 17, 2004

(54) NUCLEOTIDE SEQUENCES WHICH CODE FOR THE RODA PROTEIN

(75) Inventors: Mike Farwick, Bielefeld (DE); Klaus Huthmacher, Gelnhausen (DE); Walter Pfefferle, Halle (DE); Brigitte Bathe, Salzkotten (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/950,071

(22) Filed: Sep. 12, 2001

(65) Prior Publication Data

US 2002/0051993 A1 May 2, 2002

(30) Foreign Application Priority Data

Sep. 12, 2000 (DE) .......................... 100 44 943
Jul. 6, 2001 (DE) .......................... 101 32 947

(51) Int. Cl.$^7$ ............................. C12P 21/06
(52) U.S. Cl. ................ 435/69.1; 435/106; 435/115; 435/252.3; 435/252.32; 435/320.1; 530/350; 536/23.1
(58) Field of Search ............... 435/69.1, 106, 435/115, 252.3, 252.32, 320.1; 530/350; 536/23.1, 23.2

(56) References Cited

FOREIGN PATENT DOCUMENTS

| EP | 0 219 027 | 4/1987 |
|---|---|---|
| EP | 1 108 790 | 6/2001 |
| WO | WO 01/04325 | 1/2001 |

OTHER PUBLICATIONS

Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Yum et al. Accession AB018544. Feb. 6, 1999. (Alignment No. 1).*
N. Miller, et al., "The Sequence of H. Sapiens Cosmid Clone Luca12", Aug. 26, 1997, EMBL/Genbank/DDBJ Database, XP–002184236.
D. O. Sanchez, et al., "Gene Discovery Through Genomic Sequencing Survey of the Brucella Abortus Genome", Mar. 23, 2000, Database, XP–002184237.
R. Krämer, Genetic and Physiological Approaches for the Production of Amino Acids, *Journal of Biotechnology*, 1996, vol. 45, pp. 1–21.
B. J. Eikmanns, et al., "Molecular Aspects of Lysine, Threonine, and Isoleucine Biosynthesis in *Corynebacterium glutamicum*", Antonie Van Leeuwenhoek, Dordrecht, Netherlands, 1993, vol. 64, No. 2, pp. 145–163 (XP000918559).

* cited by examiner

Primary Examiner—Ponnathapura Achutamurthy
Assistant Examiner—Christian L Fronda
(74) Attorney, Agent, or Firm—Oblon, Spivak, McClelland, Maier & Neustadt, P.C.

(57) ABSTRACT

The invention provides nucleotide sequences from Coryneform bacteria which code for the RodA protein and a process for the fermentative preparation of amino acids using bacteria in which the rodA gene is enhanced.

27 Claims, 2 Drawing Sheets

Figure 1: Map of the plasmid pEC-XK99E
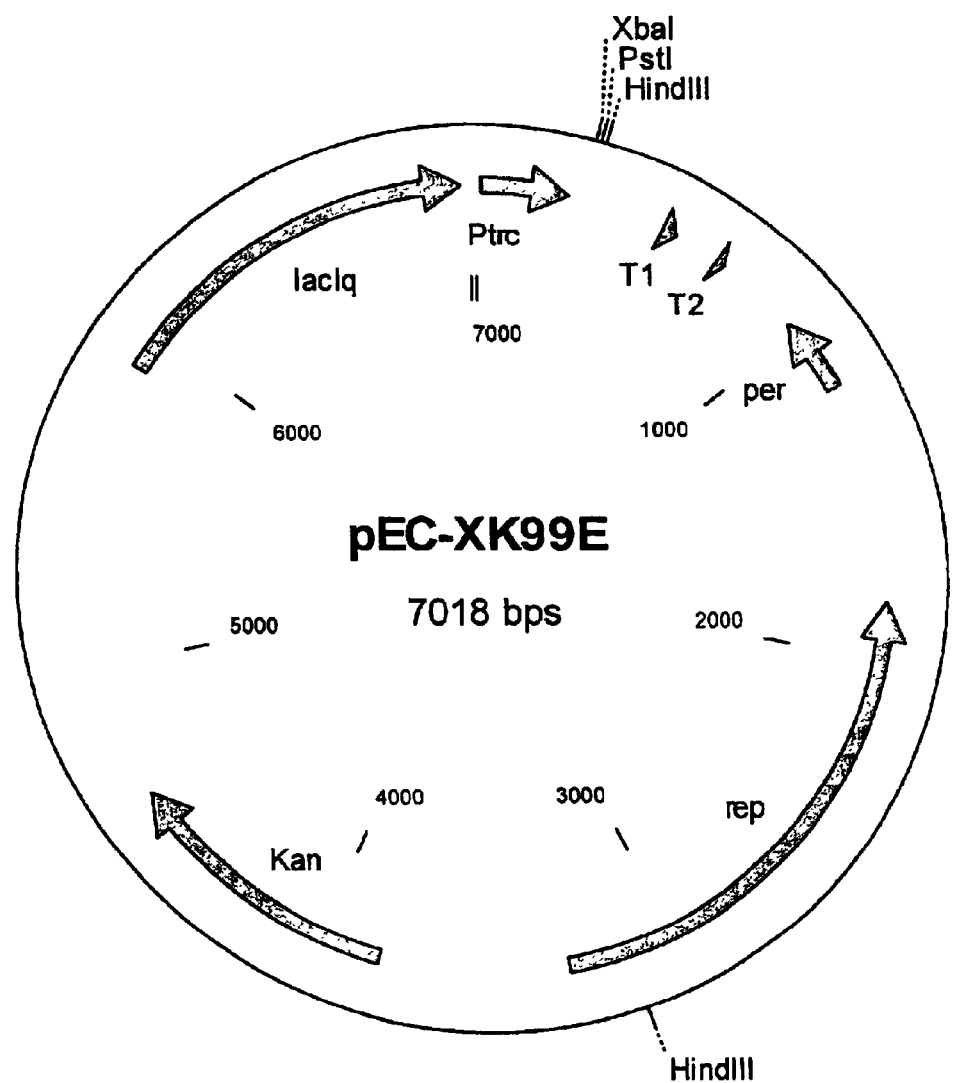

Figure 2: Map of the plasmid pEC-XK99ErodAa1ex
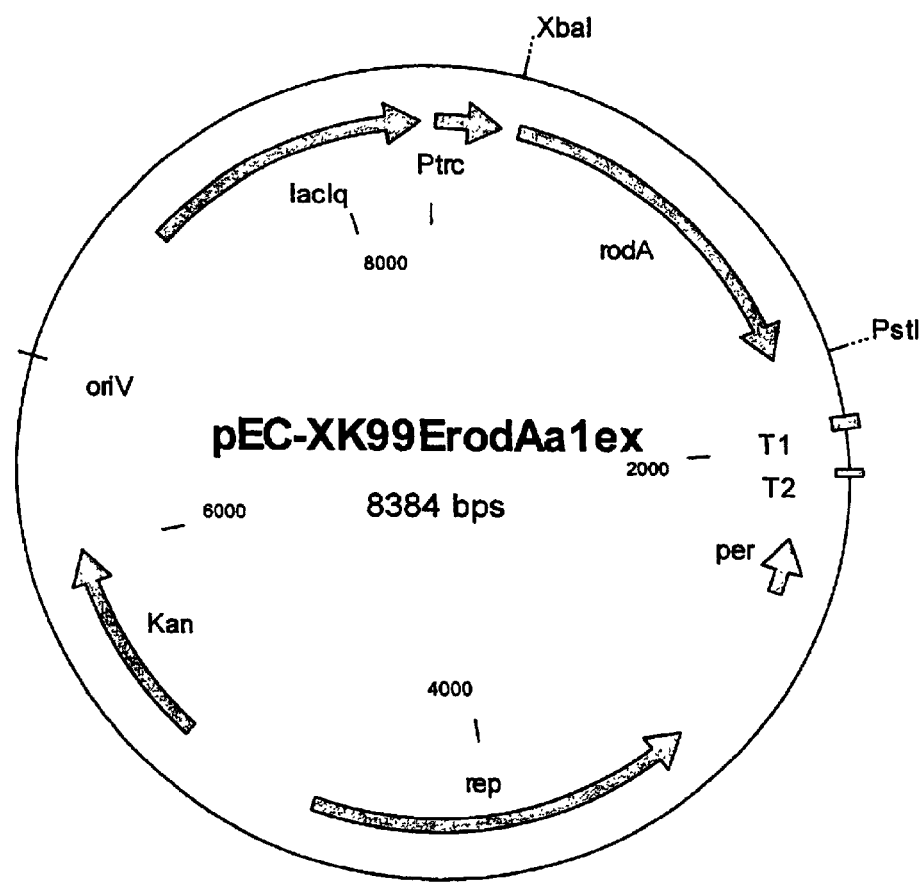

SEQUENCE LISTING

```
<160> NUMBER OF SEQ ID NOS: 4

<210> SEQ ID NO 1
<211> LENGTH: 1761
<212> TYPE: DNA
<213> ORGANISM: Corynebacterium glutamicum
<220> FEATURE:
<221> NAME/KEY: CDS
<222> LOCATION: (238)..(1560)
<223> OTHER INFORMATION:

<400> SEQUENCE: 1
gaatgaagct ggcaccttgt cactcaagga atcctgtgaa aacggtacgt ctttcaaatt      60
ggatgattta ccggcatctg ttcgcggtag tgtcgcagga ttaccgtctg ggtcgtatga     120
cgaggtccag gcgcaaatgc aacggctggc tgctcaagct ttgccagtgt gcgtgaactt     180
agaagtaaca accggtggcg atagaaacga acccggagtc aattgtaggg aggtctc       237 atg aac acg ctt gaa cga tta aag ctt cgt cgc acg gaa atg tgg ctg      285
Met Asn Thr Leu Glu Arg Leu Lys Leu Arg Arg Thr Glu Met Trp Leu
1               5                   10                  15 ctg ata ctt gcc aca ctc gtt gtg tcg atc atg ttc atc agc ctc gag      333
Leu Ile Leu Ala Thr Leu Val Val Ser Ile Met Phe Ile Ser Leu Glu
            20                  25                  30 ctg gcc atg ggc aat gag ttg ggt acc cat att ttg atg ctg atg ggc      381
Leu Ala Met Gly Asn Glu Leu Gly Thr His Ile Leu Met Leu Met Gly
        35                  40                  45 gga tat atc ggt atc ttc atc gtc gcg cac cta gcc atg gca tgg gtg      429
Gly Tyr Ile Gly Ile Phe Ile Val Ala His Leu Ala Met Ala Trp Val
    50                  55                  60 gcg ccg ttt gct gat caa atc atg ctg cct gtg gtg gcg gtg ctc aat      477
Ala Pro Phe Ala Asp Gln Ile Met Leu Pro Val Val Ala Val Leu Asn
65                  70                  75                  80 ggc att ggt ttg gtg atg att tat cgc ctt gat gag gcc acg ggc tac      525
Gly Ile Gly Leu Val Met Ile Tyr Arg Leu Asp Glu Ala Thr Gly Tyr
                85                  90                  95 agc acg gtc aat agc caa ttg atg tgg acg gtt gtt ggc gtc acg ctg      573
```

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Ser | Thr | Val | Asn | Ser | Gln | Leu | Met | Trp | Thr | Val | Val | Gly | Val | Thr | Leu |      |
|     |     |     | 100 |     |     |     |     | 105 |     |     |     |     | 110 |     |     |      |

| atg | gtg | gct | gtg | ttg | ttg | ctg | ttg | cgt | gat | tac | aag | tcg | ctt | tcg | cgt | 621  |
|-----|-----|-----|-----|-----|-----|-----|-----|-----|-----|-----|-----|-----|-----|-----|-----|------|
| Met | Val | Ala | Val | Leu | Leu | Leu | Leu | Arg | Asp | Tyr | Lys | Ser | Leu | Ser | Arg |      |
|     |     |     | 115 |     |     |     |     | 120 |     |     |     |     | 125 |     |     |      |

| tat | tcc | tac | ctc | ctc | ggt | gtg | gtg | ggc | atc | gtg | ctg | ctg | gcg | ctg | cct | 669  |
| Tyr | Ser | Tyr | Leu | Leu | Gly | Val | Val | Gly | Ile | Val | Leu | Leu | Ala | Leu | Pro |      |
|     | 130 |     |     |     |     | 135 |     |     |     |     | 140 |     |     |     |     |      |

| ctc | gtg | tgg | ccg | cag | cca | ggc | ggc | gtg | gaa | gcc | cgc | atc | tgg | att | tgg | 717  |
| Leu | Val | Trp | Pro | Gln | Pro | Gly | Gly | Val | Glu | Ala | Arg | Ile | Trp | Ile | Trp |      |
| 145 |     |     |     |     | 150 |     |     |     |     | 155 |     |     |     |     | 160 |      |

| ctt | gga | cct | ttc | tcc | atc | cag | cca | ggt | gag | ttc | tcc | aag | att | ttg | ctg | 765  |
| Leu | Gly | Pro | Phe | Ser | Ile | Gln | Pro | Gly | Glu | Phe | Ser | Lys | Ile | Leu | Leu |      |
|     |     |     |     | 165 |     |     |     |     | 170 |     |     |     |     | 175 |     |      |

| ctg | ctg | ttc | ttt | gct | cag | ctg | cta | gcc | acc | aag | cgt | gct | ttg | ttt | act | 813  |
| Leu | Leu | Phe | Phe | Ala | Gln | Leu | Leu | Ala | Thr | Lys | Arg | Ala | Leu | Phe | Thr |      |
|     |     |     | 180 |     |     |     |     | 185 |     |     |     |     | 190 |     |     |      |

| gtt | gcg | ggc | tac | cgt | ttc | ctc | ggc | atg | gat | ttc | cct | cgt | ttg | cgt | gac | 861  |
| Val | Ala | Gly | Tyr | Arg | Phe | Leu | Gly | Met | Asp | Phe | Pro | Arg | Leu | Arg | Asp |      |
|     |     | 195 |     |     |     |     | 200 |     |     |     |     | 205 |     |     |     |      |

| ctc | gcg | ccg | att | ctt | gtg | gtg | tgg | gcg | ttg | gct | att | ttg | atc | atg | gct | 909  |
| Leu | Ala | Pro | Ile | Leu | Val | Val | Trp | Ala | Leu | Ala | Ile | Leu | Ile | Met | Ala |      |
|     | 210 |     |     |     |     | 215 |     |     |     |     | 220 |     |     |     |     |      |

| ggc | gcc | aac | gac | ttc | ggt | cct | gca | ctg | ctg | ctt | ttc | act | acc | gtt | ttg | 957  |
| Gly | Ala | Asn | Asp | Phe | Gly | Pro | Ala | Leu | Leu | Leu | Phe | Thr | Thr | Val | Leu |      |
| 225 |     |     |     |     | 230 |     |     |     |     | 235 |     |     |     |     | 240 |      |

| gcc | atg | gtg | tac | ctg | gct | acc | ggc | cgt | ggt | tcc | tgg | ctg | ttg | att | ggt | 1005 |
| Ala | Met | Val | Tyr | Leu | Ala | Thr | Gly | Arg | Gly | Ser | Trp | Leu | Leu | Ile | Gly |      |
|     |     |     |     | 245 |     |     |     |     | 250 |     |     |     |     | 255 |     |      |

| gct | gtg | ttg | gtg | gct | gtc | ggc | gcg | ttc | gcg | gtg | tac | caa | gtt | tca | agc | 1053 |
| Ala | Val | Leu | Val | Ala | Val | Gly | Ala | Phe | Ala | Val | Tyr | Gln | Val | Ser | Ser |      |
|     |     |     | 260 |     |     |     |     | 265 |     |     |     |     | 270 |     |     |      |

| aag | att | cag | gaa | cgc | gtg | caa | aac | ttc | gtg | gat | cct | gtg | gcc | cac | tat | 1101 |
| Lys | Ile | Gln | Glu | Arg | Val | Gln | Asn | Phe | Val | Asp | Pro | Val | Ala | His | Tyr |      |
|     |     | 275 |     |     |     |     | 280 |     |     |     |     | 285 |     |     |     |      |

| gac | acc | acc | ggt | tac | cag | ctg | tcc | cag | tcc | ttg | ttt | ggc | atg | agt | tgg | 1149 |
| Asp | Thr | Thr | Gly | Tyr | Gln | Leu | Ser | Gln | Ser | Leu | Phe | Gly | Met | Ser | Trp |      |
|     | 290 |     |     |     |     | 295 |     |     |     |     | 300 |     |     |     |     |      |

| ggc | gga | atc | acc | ggc | acc | ggc | att | ggt | cag | ggt | tac | ccc | aac | atg | atc | 1197 |
| Gly | Gly | Ile | Thr | Gly | Thr | Gly | Ile | Gly | Gln | Gly | Tyr | Pro | Asn | Met | Ile |      |
| 305 |     |     |     |     | 310 |     |     |     |     | 315 |     |     |     |     | 320 |      |

| cct | gtc | gtg | cac | tcg | gac | ttc | att | ctc | gca | gcc | att | ggt | gag | gag | ctt | 1245 |
| Pro | Val | Val | His | Ser | Asp | Phe | Ile | Leu | Ala | Ala | Ile | Gly | Glu | Glu | Leu |      |
|     |     |     |     | 325 |     |     |     |     | 330 |     |     |     |     | 335 |     |      |

| ggt | ctg | att | ggc | ctg | gcg | gcc | atc | atc | gtg | ctg | ttt | ggt | gtg | ttt | gtc | 1293 |
| Gly | Leu | Ile | Gly | Leu | Ala | Ala | Ile | Ile | Val | Leu | Phe | Gly | Val | Phe | Val |      |
|     |     |     | 340 |     |     |     |     | 345 |     |     |     |     | 350 |     |     |      |

| acc | cgc | ggt | atg | cgc | acc | gct | acc | ctg | gct | cgt | gac | agc | tac | gga | aag | 1341 |
| Thr | Arg | Gly | Met | Arg | Thr | Ala | Thr | Leu | Ala | Arg | Asp | Ser | Tyr | Gly | Lys |      |
|     |     | 355 |     |     |     |     | 360 |     |     |     |     | 365 |     |     |     |      |

| ctc | gtg | gca | tct | ggt | ctg | tcg | atg | acc | atc | atg | atc | cag | att | ttc | gtc | 1389 |
| Leu | Val | Ala | Ser | Gly | Leu | Ser | Met | Thr | Ile | Met | Ile | Gln | Ile | Phe | Val |      |
|     | 370 |     |     |     |     | 375 |     |     |     |     | 380 |     |     |     |     |      |

| gtc | gtg | gca | ggt | att | tct | tca | ctg | atg | ccc | atg | aca | ggt | ttg | acc | act | 1437 |
| Val | Val | Ala | Gly | Ile | Ser | Ser | Leu | Met | Pro | Met | Thr | Gly | Leu | Thr | Thr |      |
| 385 |     |     |     |     | 390 |     |     |     |     | 395 |     |     |     |     | 400 |      |

| ccg | ttt | atg | tcc | cag | ggt | ggt | tca | tcc | ctg | atg | gct | aac | tac | att | ctg | 1485 |
| Pro | Phe | Met | Ser | Gln | Gly | Gly | Ser | Ser | Leu | Met | Ala | Asn | Tyr | Ile | Leu |      |
|     |     |     |     | 405 |     |     |     |     | 410 |     |     |     |     | 415 |     |      |

-continued

```
atg gcc atc atc ttg cgt att tct gac agt gcc cgc cga cct gtc atg      1533
Met Ala Ile Ile Leu Arg Ile Ser Asp Ser Ala Arg Arg Pro Val Met
        420                 425                 430 tcc aag caa gca tcg gag gtg gct gcg tgaaccgctc gattcgaatc             1580
Ser Lys Gln Ala Ser Glu Val Ala Ala
        435                 440 acatccctct tctctttgct cctgatcttg gtgctcgtag caaacctcac ctggattcag     1640
gcttttaggg acgatgatct tgctcagaac ccactgaacg cacgtggttt cctggaggcg     1700
aagtccactc cgcgtggaca gatttcaact ggtggccaag tactcgcaga gtcctcccag     1760
g                                                                     1761
```

<210> SEQ ID NO 2
<211> LENGTH: 441
<212> TYPE: PRT
<213> ORGANISM: Corynebacterium glutamicum

<400> SEQUENCE: 2

```
Met Asn Thr Leu Glu Arg Leu Lys Leu Arg Arg Thr Glu Met Trp Leu
 1               5                  10                  15

Leu Ile Leu Ala Thr Leu Val Val Ser Ile Met Phe Ile Ser Leu Glu
            20                  25                  30

Leu Ala Met Gly Asn Glu Leu Gly Thr His Ile Leu Met Leu Met Gly
        35                  40                  45

Gly Tyr Ile Gly Ile Phe Ile Val Ala His Leu Ala Met Ala Trp Val
    50                  55                  60

Ala Pro Phe Ala Asp Gln Ile Met Leu Pro Val Val Ala Val Leu Asn
65                  70                  75                  80

Gly Ile Gly Leu Val Met Ile Tyr Arg Leu Asp Glu Ala Thr Gly Tyr
                85                  90                  95

Ser Thr Val Asn Ser Gln Leu Met Trp Thr Val Val Gly Val Thr Leu
            100                 105                 110

Met Val Ala Val Leu Leu Leu Arg Asp Tyr Lys Ser Leu Ser Arg
        115                 120                 125

Tyr Ser Tyr Leu Leu Gly Val Val Gly Ile Val Leu Ala Leu Pro
    130                 135                 140

Leu Val Trp Pro Gln Pro Gly Val Glu Ala Arg Ile Trp Ile Trp
145                 150                 155                 160

Leu Gly Pro Phe Ser Ile Gln Pro Gly Glu Phe Ser Lys Ile Leu Leu
                165                 170                 175

Leu Leu Phe Phe Ala Gln Leu Leu Ala Thr Lys Arg Ala Leu Phe Thr
            180                 185                 190

Val Ala Gly Tyr Arg Phe Leu Gly Met Asp Phe Pro Arg Leu Arg Asp
        195                 200                 205

Leu Ala Pro Ile Leu Val Val Trp Ala Leu Ala Ile Leu Ile Met Ala
    210                 215                 220

Gly Ala Asn Asp Phe Gly Pro Ala Leu Leu Leu Phe Thr Thr Val Leu
225                 230                 235                 240

Ala Met Val Tyr Leu Ala Thr Gly Arg Gly Ser Trp Leu Leu Ile Gly
                245                 250                 255

Ala Val Leu Val Ala Val Gly Ala Phe Ala Val Tyr Gln Val Ser Ser
            260                 265                 270

Lys Ile Gln Glu Arg Val Gln Asn Phe Val Asp Pro Val Ala His Tyr
        275                 280                 285

Asp Thr Thr Gly Tyr Gln Leu Ser Gln Ser Leu Phe Gly Met Ser Trp
```

-continued

```
                    290                 295                 300
Gly Gly Ile Thr Gly Thr Gly Ile Gly Gln Gly Tyr Pro Asn Met Ile
305                 310                 315                 320

Pro Val Val His Ser Asp Phe Ile Leu Ala Ala Ile Gly Glu Glu Leu
                325                 330                 335

Gly Leu Ile Gly Leu Ala Ala Ile Ile Val Leu Phe Gly Val Phe Val
                340                 345                 350

Thr Arg Gly Met Arg Thr Ala Thr Leu Ala Arg Asp Ser Tyr Gly Lys
                355                 360                 365

Leu Val Ala Ser Gly Leu Ser Met Thr Ile Met Ile Gln Ile Phe Val
        370                 375                 380

Val Val Ala Gly Ile Ser Ser Leu Met Pro Met Thr Gly Leu Thr Thr
385                 390                 395                 400

Pro Phe Met Ser Gln Gly Gly Ser Ser Leu Met Ala Asn Tyr Ile Leu
                405                 410                 415

Met Ala Ile Ile Leu Arg Ile Ser Asp Ser Ala Arg Arg Pro Val Met
                420                 425                 430

Ser Lys Gln Ala Ser Glu Val Ala Ala
        435                 440

<210> SEQ ID NO 3
<211> LENGTH: 28
<212> TYPE: DNA
<213> ORGANISM: Artificial Sequence
<220> FEATURE:
<223> OTHER INFORMATION: synthetic DNA

<400> SEQUENCE: 3
gatctagagt caattgtagg gaggtctc                                          28

<210> SEQ ID NO 4
<211> LENGTH: 28
<212> TYPE: DNA
<213> ORGANISM: Artificial Sequence
<220> FEATURE:
<223> OTHER INFORMATION: synthetic DNA

<400> SEQUENCE: 4
ctctgcagga gggatgtgat tcgaatcg                                          28
```

NUCLEOTIDE SEQUENCES WHICH CODE FOR THE RODA PROTEIN

CROSS-REFERENCE TO RELATED APPLICATIONS

The present application claims priority to German Application No. DE 100 44 943.3, which was filed on Sep. 12, 2000 and German Application No. DE 101 32 947.4, which was filed on Jul. 6, 2001; the entire contents of both documents are incorporated herein by reference.

BACKGROUND OF THE INVENTION

1. Field of the Invention

The invention provides nucleotide sequences from Coryneform bacteria which code for the RodA protein and a process for the fermentative preparation of amino acids using bacteria in which the rodA gene is enhanced.

2. Discussion of the Background

L-Amino acids, in particular L-lysine, are used in human medicine and in the pharmaceuticals industry, in the foodstuffs industry and, particularly, in animal nutrition.

It is known that amino acids are prepared by fermentation from strains of Coryneform bacteria, in particular *Corynebacterium glutamicum*. Because of their great importance, work is constantly being undertaken to improve amino acid preparation processes. Improvements to the process can relate to fermentation measures, such as, stirring and supply of oxygen; the composition of the nutrient media, such as, the sugar concentration during the fermentation; o working up to the product form with, for example, ion exchange chromatography,; or altering the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of Corynebacterium strains which produce L-amino acids, by amplifying individual amino acid biosynthesis genes and investigating the effect on the amino acid production.

However, there remains a critical need for improved methods of producing L-amino acids and thus for the provision of strains of bacteria producing higher amounts of L-amino acids. On a commercial or industrial scale even small improvements in the yield of L-amino acids, or the efficiency of their production, are economically significant. Prior to the present invention, it was not recognized that attenuation of the rodA gene encoding the cell division protein RodA would improve L-amino acid yields.

SUMMARY OF THE INVENTION

An object of the present invention is to provide novel measures for the improved production of L-amino acids or amino acid, where these amino acids include L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan, L-arginine and the salts (monohydrochloride or sulfate) thereof.

One object of the present invention is providing a novel process for improving the fermentative production of said L-amino acids, particularly L-lysine. Such a process includes enhanced bacteria, preferably enhanced Coryneform bacteria, which express enhanced amounts of a RodA cell division protein or protein that has RodA protein activity.

Thus, another object of the present invention is providing such a bacterium, which expresses enhanced amounts of a RodA protein or gene products of the rodA gene.

Another object of the present invention is providing a bacterium, preferably a Coryneform bacterium, which expresses a polypeptide that has enhnaced RodA protein activity.

Another object of the invention is to provide a nucleotide sequence encoding a polypeptide having the RodA protein sequence. One embodiment of such a sequence is the nucleotide sequence of SEQ ID NO:1.

A further object of the invention is a method of making RodA protein or an isolated polypeptide having the activity of RodA, as well as use of such isolated polypeptides in the production of amino acids. One embodiment of such a polypeptide is the polypeptide having the amino acid sequence of SEQ ID NO:2.

Other objects of the invention include methods of detecting nucleic acid sequences homologous to SEQ ID NO:1, particularly nucleic acid sequences encoding polypeptides that have the activity of RodA, and methods of making nucleic acids encoding such polypeptides.

The above objects highlight certain aspects of the invention. Additional objects, aspects and embodiments of the invention are found in the following detailed description of the invention.

BRIEF DESCRIPTION OF THE DRAWINGS

FIG. 1: Map of the plasmid pEC-XK99E

FIG. 2: Map of the plasmid pEC-XK99ErodAalex

DETAILED DESCRIPTION OF THE INVENTION

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Cold Spring Harbor Laboratory, New York (1989), Current Protocols in Molecular Biology, Ausebel et al (eds), John Wiley and Sons, Inc. New York (2000)and the various references cited therein.

"L-amino acids" or "amino acids" as used herein means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. L-Lysine is particularly preferred.

When L-lysine or lysine are mentioned in the following, not only the bases but also the salts, such as e.g. lysine monohydrochloride or lysine sulfate, are meant by this.

The invention provides an isolated polynucleotide from Coryneform bacteria, comprising a polynucleotide sequence which codes for the rodA gene, chosen from the group consisting of
a) polynucleotide which is identical to the extent of at least 70% to a polynucleotide which codes for a polypeptide which comprises the amino acid sequence of SEQ ID No.2,
b) polynucleotide which codes for a polypeptide which comprises an amino acid sequence which is identical to the extent of at least 70% to the amino acid sequence of SEQ ID No.2,
c) polynucleotide which is complementary to the polynucleotides of a) or b), and;
d) polynucleotide comprising at least 15 successive nucleotides of the polynucleotide sequence of a), b) or c), the polypeptide preferably having the activity of the cell division protein RodA.

The invention also provides the above-mentioned polynucleotide, this preferably being a DNA which is capable of replication, comprising:
(i) the nucleotide sequence shown in SEQ ID No.1, or
(ii) at least one sequence which corresponds to sequence (i) within the range of the degeneration of the genetic code, or
(iii) at least one sequence which hybridizes with the sequence complementary to sequence (i) or (ii), and optionally
(iv) sense mutations of neutral function in (i).

The invention also provides
a polynucleotide, in particular DNA, which is capable of replication and comprises the nucleotide sequence as shown in SEQ ID No.1;
a polynucleotide which codes for a polypeptide which comprises the amino acid sequence as shown in SEQ ID No.2; a vector containing the polynucleotide according to the invention, in particular a shuttle vector or plasmid vector, and
Coryneform bacteria which contain the vector or in which the rodA gene is enhanced.

The invention also provides polynucleotides which substantially comprise a polynucleotide sequence, which are obtainable by means of hybridization of a corresponding gene library of a Coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

Polynucleotides which comprise the sequences according to the invention are suitable as hybridization probes for RNA, cDNA and DNA, in order to isolate, in the full length, nucleic acids or polynucleotides or genes which code for the cell division protein RodA, or to isolate those nucleic acids or polynucleotides or genes which have a high similarity of sequence with that of the rodA gene.

Additionally, methods employing DNA chips, microarrays or similar recombinant DNA technology that enables high throughput screening of DNA and polynucleotides which encode the RodA protein or polynucleotides with homology to the rodA gene as described herein. Such methods are known in the art and are described, for example, in Current Protocols in Molecular Biology, Ausebel et al (eds), John Wiley and Sons, Inc. New York (2000).

Polynucleotides which comprise the sequences according to the invention are furthermore suitable as primers with the aid of which DNA of genes which code for the cell division protein RodA can be prepared by the polymerase chain reaction (PCR).

Such oligonucleotides which serve as probes or primers comprise at least 25, 26, 27, 28, 29 or 30, preferably at least 20, 21, 22, 23 or 24, very particularly preferably at least 15, 16, 17, 18 or 19 successive nucleotides. Oligonucleotides with a length of at least 31, 32, 33, 34, 35, 36, 37, 38, 39 or 40, or at least 41, 42, 43, 44, 45, 46, 47, 48, 49 or 50 nucleotides are also suitable. Oligonucleotides with a length of at least 100, 150, 200, 250 or 300 nucleotides are optionally also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No.1 or a fragment prepared therefrom and also those which are at least 70% to 80%, preferably at least 81% to 85%, particularly preferably at least 86% to 90%, and very particularly preferably at least 91%, 93%, 95%, 97% or 99% identical to the polynucleotide according to SEQ ID No.1 or a fragment prepared therefrom.

"Polypeptides" are understood as meaning peptides or proteins which comprise two or more amino acids bonded via peptide bonds.

The polypeptides according to the invention include a polypeptide according to SEQ ID No.2, in particular those with the biological activity of the cell division protein RodA and also those which are at least 70% to 80%, preferably at least 81% to 85%, particularly preferably at least 86% to 90%, and very particularly preferably at least 91%, 93%, 95%, 97% or 99% identical to the polypeptide according to SEQ ID No.2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using Coryneform bacteria which in particular already produce amino acids and in which the nucleotide sequences which code for the rodA gene are enhanced, in particular over-expressed.

The term "enhancement" in this connection describes the increase in the intracellular activity of one or more enzymes (proteins) in a microorganism which are coded by the corresponding DNA, for example by increasing the number of copies of the gene or genes, using a potent promoter or using a gene or allele which codes for a corresponding enzyme (protein) having a high activity, and optionally combining these measures.

By enhancement measures, in particular over-expression, the activity or concentration of the corresponding protein is in general increased by at least 10%, 25%, 50%, 75%, 100%, 150%, 200%, 300%, 400% or 500%, up to a maximum of 1000% or 2000%, based on that of the wild-type protein or the activity or concentration of the protein in the starting microorganism.

The microorganisms which the present invention provides can produce L-amino acids from glucose, sucrose, lactose, fructose, maltose, molasses, starch, cellulose or from glycerol and ethanol. They can be representatives of Coryneform bacteria, in particular of the genus Corynebacterium. Of the genus Corynebacterium, there may be mentioned in particular the species *Corynebacterium glutamicum*, which is known among experts for its ability to produce L-amino acids.

Suitable strains of the genus Corynebacterium, in particular of the species *Corynebacterium glutamicum* (*C. glutamicum*), are in particular the known wild-type strains

*Corynebacterium glutamicum* ATCC 13032
*Corynebacterium acetoglutamicum* ATCC 15806
*Corynebacterium acetoacidophilum* ATCC 13870
*Corynebacterium thermoaminogenes* FERM BP-1539
*Corynebacterium melassecola* ATCC 17965
*Brevibacterium flavum* ATCC 14067
*Brevibacterium lactofermentum* ATCC13869 and
*Brevibacterium divaricatum* ATCC14020 and L-amino acid-producing mutants or strains prepared therefrom.

Preferably, a bacterial strain with enhanced expression of a rodA gene that encodes a polypeptide with RodA protein activity will improve amino acid yield at least 1%.

The new rodA gene from *C. glutamicum* which codes for the cell division protein RodA has been isolated.

To isolate the rodA gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene and Klone, Eine Einführung in die Gentechnologie [Genes and Clones, An Introduction to Genetic Engineering] (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in k vectors by Kohara et al. (Cell 50, 495–508 (1987)). Bathe et al. (Molecular and General Genetics, 252:255–265, 1996) describe a gene library of *C. glutamicum* ATCC 13032, which was set up with the aid of the cosmid vector SuperCos I (Wahl et al., 1987, Proceedings of the National Academy of Sciences USA, w 84:2160–2164) in the *E. coli* K-12 strain NM554 (Raleigh et al., 1988, Nucleic Acids Research 16:1563–1575).

Börmann et al. (Molecular Microbiology 6(3), 317-326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination- defective. An example of these is the strain DH5αmcr, which has been described by Grant et al. (Proceedings of the National Academy of Sciences USA, 87 (1990) 4645–4649).

The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829 1836 (1988)) or the GCG program of Butler (Methods of Biochemical Analysis 39, 74–97 (1998)).

The new DNA sequence of *C. glutamicum* which codes for the rodA gene and which, as SEQ ID No.1, is a constituent of the present invention has been found. The amino acid sequence of the corresponding protein has furthermore been derived from the present DNA sequence by the methods described above. The resulting amino acid sequence of the rodA gene product is shown in SEQ ID No.2.

Coding DNA sequences which result from SEQ ID No.1 by the degeneracy of the genetic code are also a constituent of the invention. In the same way, DNA sequences which hybridize with SEQ ID No.1 or parts of SEQ ID No.1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No.2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al (International Journal of Systematic Bacteriology (1991) 41: 255–260). The hybridization takes place under stringent conditions, that is to say only hybrids in which the probe and target sequence, i.e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50° C.–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50° C.–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50° C. to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

It has been found that Coryneform bacteria produce amino acids in an improved manner after over-expression of the rodA gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the mRNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in EP 0 472 869, in U.S. Pat. No. 4,601,893, in Schwarzer and Puhler (Bio/Technology 9, 84–87 (1991)), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the rodA gene according to the invention was over-expressed with the aid of episomal plasmids. Suitable plasmids are those which are replicated in Coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (US-A 4,489, 160), or pNG2 (Serwold-Davis et al., FEMS Microbiology Letters 66, 119–124 (1990)), or pAG1 (U.S. Pat. No. 5,158, 891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schafer et al., Gene 145, 6973 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector which contains the gene to be amplified is then transferred into the desired strain of C. glutamicum by conjugation or transformation. The method of conjugation is described, for example, by Schafer et al. (Applied and Environmental Microbiology 60, 756–759 (1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of L-amino acids to enhance, in particular over-express one or more enzymes of the particular biosynthesis pathway, of glycolysis, of anaplerosis, of the citric acid cycle, of the pentose phosphate cycle, of amino acid export and optionally regulatory proteins, in addition to the roda gene.

Thus, for the preparation of L-amino acids, in addition to enhancement of the rodA gene, one or more genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A198 31 609), the mqo gene which codes for malate-quinone oxidoreductase (Molenaar et al., European Journal of Biochemistry 254, 395–403 (1998)), the lysC gene which codes for a feed-back resistant aspartate kinase (Accession No.P26512; EP-B-0387527; EPA-0699759), the lysE gene which codes for lysine export (DE-A-195 48 222), the hom gene which codes for homoserine dehydrogenase (EP-A 0131171), the ilvA gene which codes for threonine dehydratase (Mockel et al., Journal of Bacteriology (1992) 80658072)) or the ilvA(Fbr) allele which codes for a "feed back resistant" threonine dehydratase (Mockel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein. (DE: 19959328.0, DSM 13115), can be enhanced, in particular over-expressed.

It may furthermore be advantageous for the production of L-amino acids, in addition to the enhancement of the rodA gene, for one or more genes chosen from the group consisting of:

the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7; DSM 13114), the zwa2 gene which codes for the Zwa2 protein (DE: 19959327.2, DSM 13113)

to be attenuated, in particular for the expression thereof to be reduced.

The term "attenuation" in this connection describes the reduction or elimination of the intracellular activity of one or more enzymes (proteins) in a microorganism which are coded by the corresponding DNA, for example by using a weak promoter or using a gene or allele which codes for a corresponding enzyme with a low activity or inactivates the corresponding gene or enzyme (protein), and optionally combining these measures.

By attenuation measures, the activity or concentration of the corresponding protein is in general reduced to 0 to 75%, 0 to 50%, 0 to 25%, 0 to 10% or 0 to 5% of the activity or concentration of the wild-type protein or of the activity or concentration of the protein in the starting microorganism.

In addition to over-expression of the rodA gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik [Bioprocess Technology 1. Introduction to Bioprocess Technology (Gustav Fischer Verlag, Stuttgart, 1991)) or in the textbook by Storhas (Bioreaktoren and periphere Einrichtungen [Bioreactors and Peripheral Equipment] (Vieweg Verlag, Braunschweig/Wiesbaden, 1994)). The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substance can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium containing salts can be used as the source of phosphorus. The culture medium must furthermore comprise salts of metals, such as e.g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51:11671174).

The process according to the invention is used for fermentative preparation of amino acids.

The present invention is explained in more detail in the following with the aid of embodiment examples.

The following microorganism was deposited as a pure culture on May 18th 2001 at the Deutsche Sammlung für Mikroorganismen and Zellkulturen (DSMZ=German Collection of Microorganisms and Cell Cultures, Braunschweig, Germany) in accordance with the Budapest Treaty:

*Escherichia coli* DHSamcr/pEC-XK99ErodAalex as DSM 14312.

The isolation of plasmid DNA from *Escherichia coli* and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA). Methods for transformation of *Escherichia coli* are also described in this handbook.

The composition of the usual nutrient media, such as LB or TY medium, can also be found in the handbook by Sambrook et al.

Having generally described this invention, a further understanding can be obtained by reference to certain specific examples which are provided herein for purposes of illustration only, and are not intended to be limiting unless otherwise specified.

EXAMPLES

Example 1

Preparation of a genomic cosmid gene library from *Corynebacterium glutamicum* ATCC 13032

Chromosomal DNA from *Corynebacterium glutamicum* ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved a with the restriction enzyme XbaI (Amersham Pharmacia, Freiburg, Germany, Product Description XbaI, Code no. 270948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNALigase, Code no.27-0870-04). The ligation mixture was then packed in phages with the aid of Gigapack II XL Packing Extract (Stratagene, La Jolla, USA, Product Description Gigapack II XL Packing Extract, Code no. 200217).

For infection of the *E. coli* strain NM554 (Raleigh et al. 1988, Nucleic Acid Research 16:1563–1575) the cells were taken up in 10 MM MgS04 and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/1 ampicillin. After incubation overnight at 37° C., recombinant individual clones were selected.

Example 2

Isolation and sequencing of the rodA gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 by were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-O1), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 lipase (Pharmacia Biotech, Freiburg, Germany). This ligation mixture was then electroporated (Tauch et al. 1994, FEMS Microbiol Letters, 123:343–7) into the *E. coli* strain DH5αMCR (Grant, 1990, Proceedings of the National Academy of Sciences U.S.A., 87:4645–4649) and plated out on LB agar (Lennox, 1955, Virology, 1:190) with 50 mg/1 zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No.

A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pZeroI derivatives were assembled to a continuous contig. The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 1326 base pairs, which was called the rodA gene. The rodA gene codes for a protein of 441 amino acids.

Example 3

Preparation of the shuttle expression vector pEC-XK99ErodAalex for enhancement of the roda gene in *C. glutamicum*

3.1 Cloning of the rodA gene

From the strain ATCC 13032, chromosomal DNA was isolated by the method of Eikmanns et al. (Microbiology 140:1817–1828 (1994)). On the basis of the sequence of the rodA gene known for *C. glutamicum* from example 2, the following oligonucleotides were chosen for the polymerise chain reaction (see SEQ ID No. 3 and SEQ ID No. 4):

rodAex1:

5' ga tct aga-gtc aat tgt agg gag gtc tc 3' rodAex2:

5' ct ctg cag-gag gga tgt gat tcg aat cg 3'

The primers shown were synthesized by MWG-Biotech AG (Ebersberg, Germany) and the PCR reaction was carried out by the standard PCR method of Innis et al. (PCR protocols. A guide to methods and applications, 1990, Academic Press) with Pwo-Polymerise from Roche Diagnostics GmbH (Mannheim, Germany). With the aid of the polymerise chain reaction, the primers allow amplification of a DNA fragment 1388 by in size, which carries the rodA gene. Furthermore, the primer rodAex1 contains the sequence for the cleavage site of the restriction endonuclease XbaI, and the primer rodAex2 the cleavage site of the restriction endonuclease PstI, which are marked by underlining m the nucleotide sequence shown above.

The rodA fragment 1388 by in size was cleaved with the restriction endonucleases XbaI and PstI and then isolated from the agarose gel with the QiaExII Gel Extraction Kit (Product No. 20021, Qiagen, Hilden, Germany).

3.2 Construction of the shuttle vector pEC-XK99E

The E. coli-C. glutamicum shuttle vector pEC-XK99E was constructed according to the prior art. The vector contains the replication region rep of the plasmid pGA1 including the replication effector per (U.S. Pat. No. 5,175,108; Nesvera et al., Journal of Bacteriology 179, 1525–1532 (1997)), the kanamycin resistance gene aph(3')-IIa from *Escherichia coli* Beck et al. (1982), Gene 19: 327–336), the replication origin of the trc promoter, the termination regions T1 and T2, the lacIq gene (repressor of the lac operon of *E. coli*) and a multiple cloning site (mcs) (Norrander, J. M. et al. Gene 26, 101–106 (1983)) of the plasmid pTRC99A (Amann et al. (1988), Gene 69: 301–315).

The *E. coli-C. glutamicum* shuttle vector pEC-XK99E constructed was transferred into *C. glutamicum* DSM5715 by means of electroporation (Liebl et al., 1989, FEMS Microbiology Letters, 53:299–303). Selection of the transformants took place on LBHIS agar comprising 18.5 g/l brain-heart infusion broth, 0.5 M sorbitol, 5 g/l Bactotryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonuclease HindIII, and the plasmid was checked by subsequent agarose gel electrophoresis.

The plasmid construct obtained in this way was called pECXK99E (FIG. 1). The strain obtained by electroporation of the plasmid pEC-XK99E in the *C. glutamicum* strain DSM5715 was called DSM5715/pEC-XK99E and deposited as DSM13455 at the Deutsche Sammlung für Mikroorganismen and Zellkulturen (DSMZ=German Collection of Microorganisms and Cell Cultures, Braunschweig, Germany) in accordance with the II Budapest Treaty.

3.3 Cloning of rodA in the *E. coli-C. glutamicum* shuttle vector pEC-XK99E

The *E. coli-C. glutamicum* shuttle vector pEC-XK99E described in example 3.2 was used as the vector. DNA of this plasmid was cleaved completely with the restriction enzymes XbaI and PstI and then dephosphorylated with shrimp alkaline phosphatase (Roche Diagnostics GmbH, Mannheim, Germany, Product Description SAP, Product No. 1758250).

The rodA fragment approx. 1380 by in size described in example 3.1, obtained by means of PCR and cleaved with the restriction enonucleases XbaI and PstI was mixed with the prepared vector pEC-XK99E and the batch was treated with T4 DNA ligase (Amersham Pharmacia, Freiburg, Germany, Product Description T4-DNA-Ligase, Code no.27-0870-04).

The ligation batch was transformed in the *E. coli* strain DH5αmcr (Hanahan, In: DNA cloning. A practical approach. Vol. I. IRL-Press, Oxford, Washington DC, USA). Selection of plasmid-carrying cells was made by plating out the transformation batch on LB agar (Lennox, 1955, Virology, 1:190) with 50 mg/l kanamycin. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes XbaI and PstI to check the plasmid by subsequent agarose gel electrophoresis. The resulting plasmid was called pEC-XK99ErodAalex. It is shown in FIG. 2.

Example 4

Transformation of the strain DSM5715 with the plasmid pEC-XK99ErodAalex

The strain DSM5715 was transformed with the plasmid pEC-XK99ErodAalex using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 25 mg/l kanamycin. Incubation was carried out for 2 days at 33° C.

Plasmid DNA was isolated from a transformant by conventional methods (Peters-Wendisch et al., 1998, Microbiology, 144, 915–927), cleaved with the restriction endonucleases XbaI and PstI, and the plasmid was checked by subsequent agarose gel electrophoresis. The strain obtained was called DSM5715/pEC-XK99ErodAalex.

Example 5

Preparation of Lysine

The *C. glutamicum* strain DSM5715/pEC-XK99ErodAalex obtained in example 4 was cultured in a nutrient medium suitable for the production of lysine and the lysine content in the culture supernatant was determined.

For this, the strain was first incubated on an agar plate with the corresponding antibiotic (brain-heart agar with kanamycin (25 mg/l)) for 24 hours at 33° C. Starting from this agar plate culture, a preculture was seeded (10 ml medium in a 100 ml conical flask). The complete medium CgIII was used as the medium for the preculture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 20% (w/v) |
| The pH was brought to pH 7.4 | |

Kanamycin (25 mg/l) was added to this. The preculture was incubated for 16 hours at 33° C. at 240 rpm on a shaking machine. A main culture was seeded from this preculture such that the initial OD (660 nm) of the main culture was 0.1. Medium MM was used for the main culture.

| Medium MM | |
|---|---|
| CSL (corn steep liquor) | 5 g/l |
| MOPS (morpholinopropanesulfonic acid) | 20 g/l |
| Glucose (autoclaved separately) | 50 g/l |
| $(NH_4)_2SO_4$ | 25 g/l t |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the CaCO$_3$ autoclaved in the dry state.

Culturing is carried out in a 10 ml volume in a 100 ml conical flask with baffles. Kanamycin (25 mg/l) was added.

Culturing was carried out at 33° C. and 80% atmospheric humidity.

After 48 hours, the OD was determined at a measurement wavelength of 660 nm with a Biomek 1000 (Beckmann Instruments GmbH, Munich). The amount of lysine formed was determined with an amino acid analyzer from Eppendorfi BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
|---|---|---|
| DSM5715 | 11.3 | 13.02 |
| DSM5715/pEC-XK99ErodAalex | 12.6 | 14.15 |

The abbreviations and designations used herein have the following meaning:

Kan: Kanamycin resistance gene aph(3')-IIa from *Escherichia coli*
HindIII Cleavage site of the restriction enzyme HindIII
XbaI Cleavage site of the restriction enzyme XbaI
PstI Cleavage site of the restriction enzyme PstI
Ptrc trc promoter
T1 Termination region T1
T2 Termination region T2
per Replication effector per
rep Replication region rep of the plasmid pGA1
lacIq lacIq repressor of the lac operon of *Escherichia coli*
rodA Cloned rodA gene Obviously, numerous modifications and variations on the present invention are possible in light of the above teachings. It is therefore to be understood that within the scope of the appended claims, the invention may be practiced otherwise than as specifically described herein.

What is claimed is:

1. An isolated polynucleotide which encodes a protein comprising the amino acid sequence of SEQ ID NO: 2, wherein said protein has the activity of the RodA cell division protein.

2. A vector comprising the isolated polynucleotide of claim 1.

3. A host cell comprising the isolated polynucleotide of claim 1.

4. The host cell of claim 3, which is a coryneform bacterium.

5. The host cell of claim 3, wherein said host cell is selected from the group consisting of *Corynebacterium glutamicum, Cotynebacterium acetoglutamicum, Corynebacterium acetoacidophilum, Corynebacterium melassecola, Corynebacterium thermoaminogenes, Brevibacterium flavum, Brevibacterium lactofermentum,* and *Brevibacterium divaricatum.*

6. A method for making a RodA protein, comprising culturing the host cell of claim 3 for a time and under conditions suitable for expression of the RodA protein; and collecting the RodA protein.

7. An isolated polynucleotide, which comprises SEQ ID NO:1 and encodes a protein which has the activity of the RodA cell division protein.

8. An isolated polynucleotide, which is complimentary to the polynucleotide of claim 7.

9. An isolated polynucleotide which comprises a fragment of the polynucleotide of claim 7 and encodes a protein which has the activity of the RodA cell division protein.

10. An isolated polynucleotide which hybridizes under stringent conditions to the polynucleotide of claim 7 or the complement thereof and encodes a protein which has the activity of the RodA cell division protein; wherein said stringent conditions comprise washing in 0.5×SSC at a temperature of 68° C.

11. A vector comprising the isolated polynucleotide of claim 7.

12. A host cell comprising the isolated polynucleotide of claim 7.

13. The host cell of claim 12, which is a coryneform bacterium.

14. The host cell of claim 12, wherein said host cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum.*

15. A method for making RodA protein, comprising a) culturing the host cell of claim 12 for a time and under conditions suitable for expression of the RodA protein; and b) collecting the RodA protein.

16. A process for producing an L-amino acid, comprising culturing the host cell of claim 13 in a medium suitable for producing the L-amino acid; and collecting the L-amino acid produced.

17. The process of claim 16, wherein said host cell is a coryneform bacterium or Brevibacterium.

18. The process of claim 17, wherein said host cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum.*

19. The process of claim 16, wherein the L-amino acid is L-lysine.

20. The process of claim 16, further comprising isolating the L-amino acid.

21. A process for producing an L-amino acid, comprising a) culturing the host cell of claim 12 in a medium suitable for producing the L-amino acid and for a time and under conditions suitable for producing the L-amino acid; and b) collecting the L-amino acid.

22. The process of claim 21, wherein said host cell is a coryneform bacterium or Brevibacterium.

23. The process of claim 22, wherein said host cell is selected from the group consisting of *Corynebacterium glutamicum, Corynebacterium acetoglutamicum, Corynebacterium acetoacidophilum, Corynebacterium melassecola, Corynebacterium thermoaminogenes, Brevibacterium flavum, Brevibacterium lactofermentum*, and *Brevibacterium divaricatum.*

24. The process of claim 21, wherein the L-amino acid is L-lysine.

25. The process of claim further comprising isolating the L-amino acid.

26. An isolated polynucleotide, consisting of at least 23 consecutive nucleotides of SEQ ID NO: 1, having the function of a primer in a polymerase chain reaction to prepare or amplify a polynucleotide encoding a protein/polypeptide having the activity of the RodA cell division protein.

27. An isolated polynucleotide consisting of at least 23 consecutive nucleotides of SEQ ID NO: 1 or the complement thereof, having the function of a probe in a hybridization reaction to isolate, detect, or determine a polynucleotide encoding a protein/polypeptide having the activity of the RodA cell division protein.

* * * * *